(12) United States Patent
Tian

(10) Patent No.: US 8,197,823 B2
(45) Date of Patent: Jun. 12, 2012

(54) VACCINE FOR PORCINE REPRODUCTIVE AND RESPIRATORY SYNDROME, A PREPARION METHOD AND USE THEREOF

(75) Inventor: Kegong Tian, Beijing (CN)

(73) Assignee: China Animal Disease Control Center, Beijing (CN)

( * ) Notice: Subject to any disclaimer, the term of this patent is extended or adjusted under 35 U.S.C. 154(b) by 351 days.

(21) Appl. No.: 12/522,484

(22) PCT Filed: Feb. 21, 2008

(86) PCT No.: PCT/CN2008/000374
§ 371 (c)(1),
(2), (4) Date: Jul. 28, 2009

(87) PCT Pub. No.: WO2008/110056
PCT Pub. Date: Sep. 18, 2008

(65) Prior Publication Data
US 2010/0068225 A1    Mar. 18, 2010

(30) Foreign Application Priority Data
Mar. 14, 2007  (CN) .......................... 2007 1 0086549

(51) Int. Cl.
*A61K 39/12*  (2006.01)
(52) U.S. Cl. ........................................ 424/204.1; 435/5

(58) Field of Classification Search .................. None
See application file for complete search history.

(56) References Cited

U.S. PATENT DOCUMENTS

| 6,110,468 | A  | * | 8/2000 | Collins et al. | ............. | 424/204.1 |
| 6,241,990 | B1 | * | 6/2001 | Collins et al. | ............. | 424/204.1 |

OTHER PUBLICATIONS

Li et al, The Veterinary Journal, Nov. 2007, Epub Sep. 14, 2007; vol. 174, pp. 577-584.*
Gao et al, Archives of Virology, 2004, vol. 149, pp. 1341-1351.*
Zhou et al, Journal of Virology, May 2009, vol. 83, No. 10, pp. 5156-5167.*

* cited by examiner

*Primary Examiner* — Ali R. Salimi
(74) *Attorney, Agent, or Firm* — Sughrue Mion, PLLC

(57) ABSTRACT

Aspects of the present inventions discloses a Super-Virulent Variant Strain of Porcine Reproductive and Respiratory Syndrome Virus, characterized in that nucleotides 1594th-1680th are deleted in its Nsp2 gene. The present invention also discloses a Vaccine prepared with the Super-Virulent Variant Strain of the Virus for prevention of Porcine Reproductive and Respiratory Syndrome. The present invention may further discloses preparations, assay methods and/or the application of the Vaccine in preparing medicaments to resist Super-Virulent Variant Strain of Porcine Reproductive and Respiratory Syndrome Virus by immunizing pigs.

5 Claims, No Drawings

VACCINE FOR PORCINE REPRODUCTIVE AND RESPIRATORY SYNDROME, A PREPARION METHOD AND USE THEREOF

TECHNICAL FIELD

The present invention relates to prevention and control of animal epidemics disease, in particular, relates to an inactivated vaccine against super-virulent variant strain of Porcine Reproductive and Respiratory Syndrome Virus (PRRSV) as well as to the preparation and application of the vaccine itself.

BACKGROUND ART

Since June 2006, "porcine high fever disease" epidemic situation broke out in pig farms and peasant households in many provinces of China. The applicant studied and found that Super-Virulent Variant Strain of Porcine Reproductive and Respiratory Syndrome Virus (Nsp2 1594th-1680th deletion variant strain) is the primary cause of "porcine high fever disease" epidemic situation and then isolated and identified the virus (Classification Name: Porcine Reproductive and Respiratory Syndrome Virus; Latin Name Porcine Reproductive and Respiratory Syndrome Virus, PRRSV; Deposit Institution China Microbiological Spawn Deposit Management Committee General Microbiological Culture Collection Center (CGMCC); Deposit Date: Mar. 9, 2007; Deposit Nos.: CGMCC No. 1964).

Porcine Reproductive and Respiratory Syndrome caused by Porcine Reproductive and Respiratory Syndrome Virus (PRRSV) is a disease with clinical features such as fever and abortion of sows, increased piglet mortality before and after weaning, and respiratory disorder in different ages of pigs. In 2006 and 2007, Porcine Reproductive and Respiratory Syndrome Virus Super-Virulent Variant Strain (Nsp2 1594th-1680th deletion variant strain), which has significantly increased pathogenicity on pigs and incurred heavy losses to pig farmers, is pandemic in China.

Since all currently available PRRSV Vaccines are not prepared in connection with the above variant strain, they can not generate protection against said variant strain. To some extent, the Inactivated Vaccine for approval at the present stage may resist the attack of PRRSV Super-Virulent Variant Strains (all inactivated Vaccines are prepared with no Super-Virulent variant strain, protective effects differ in different manufactures). In a view of the theoretic analysis, there is a need to develop a vaccine specifically aimed at Porcine Reproductive and Respiratory Syndrome Virus Super-Virulent Variant Strain (Nsp2 1594th-1680th deletion variant strain).

There are some defects in determining the efficacy of currently available PRRSV Vaccines. For example, since pathogenicity of the variant strain used (VR2332 standard variant strain) on pigs is not strong enough to lead to significant pathogenesis and death of pigs, it is difficult to evaluate the efficacy of PRRSV Vaccine based on immunity challenge protective test using the said standard strain.

CONTENTS OF THE INVENTION

Features of the present invention are to overcome the shortcomings of the prior art and provide an Inactivated Vaccine against Super-Virulent Variant Strain of Porcine Reproductive and Respiratory Syndrome Virus (PRRSV) as well as to preparation and application of the vaccine itself.

Aspects of the present invention may be carried out by the following technical solution: the Inactivated Vaccine is developed using Super-Virulent Variant Strain (Nsp2 1594th-1680th deletion variant strain) of Porcine Reproductive and Respiratory Syndrome Virus (PRRSV) for the prevention of PRRS caused by Super-Virulent Variant Strain of Porcine Reproductive and Respiratory Syndrome Virus (Nsp2 1594th-1680th deletion variant). The preliminary test result shows a good immunity protective action.

The present application relates to a virus strain: Super-Virulent Variant Strain of Porcine Reproductive and Respiratory Syndrome Virus (Nsp2 1594th-1680th deletion variant strain). Deposit information is as follows:

Classification name: Porcine Reproductive and Respiratory Syndrome Virus

Latin name: Porcine reproductive and respiratory syndrome virus, PRRSV

Deposit institution: China Microbiological Spawn Deposit Management Committee General Microbiological Culture Collection Center (CGMCC)

Address: Institute of Microbiology, Chinese Academy of Sciences, No. 13 ZhongGuanCun Bei Yi Tiao, Haidian District, Beijing Deposit Date Mar. 9, 2007

Deposit Number: CGMCC No. 1964

Physicochemical properties: the virus is 40~80 nm in diameter and spherical or oval virion with a cystmembrane. The virus can not agglutinate O phenotype erythrocytes of rhesus, pig, canine, rabbit, guinea pig, SD rat, Balb/c mouse, chicken and human.

Culture character: the virus is cultured and proliferated in the Marc-145 cells and cytopathic effect (CPE) (cell aggregation, swell, cell blurring of contour, cell rounding, shrinking, karyopyknosis, kitchen shape shedding) is generated. No CPE is produced in other five cell lines such as PK-15, ST, BHK21, VERO, MDCK.

Isolation and Identification:

The viruses are isolated in the Jiang Xi Province from the cerebral tissue of pigs that died of the disease. The sample of cerebral tissue from the pigs was inoculated on the monolayer of PK-15 cells, statically cultured at 37° C. in the incubator and observed for 7 days. The culture medium was collected when CPE occurred and preserved at −70° C.

The spherical virions which are about 50 nm in diameter and have an envelope are observed by negative staining electron microscope; The result of ultrathin-section electron microscope observation shows that lots of typical spherical, oval virions with 40~80 nm in diameter are aggregated in cytoplasm.

The virus is identified as American type PRRSV by RT-PCR and monoclonal antibody neutralization test. Complete genome sequencing result shows that the full-length of virus genome without Poly A tail is 15320 bp. Its highest homology, 96.5%, is shown with American type PRRSV HB-1(sh) strain. Comparing with American type PRRSV standard strain (VR-2332 strain), the virus strain lost nucleotides 1441st-1443rd and 1594th-1680th in its Nsp2 gene.

Pathogenicity: five piglets at 21 days old were inoculated with the virus and all five piglets caught the disease and died within 10 days. The clinical symptom and general autopsy change of the five piglets are substantially similar to those of clinically seen in the illness pigs. The virus was detected and recovered by RT-PCR and by virus isolation assay. Twenty-nine piglets were also inoculated with the virus when they were 2 months old. The morbidity is 100% and the mortality is 57%. Therefore, comparing with previous common PRRSV virus strain, the said virus showed the significantly increased pathogenicity and is named as PRRSV Super-Virulent variant strain.

A Super-Virulent Variant Strain of Porcine Reproductive and Respiratory Syndrome Virus, characterized in that nucleotides 1594th-1680th are deleted in the virus Nsp2 gene; the Virus Deposit number is: CGMCC No. 1964.

A Vaccine prepared with the Super-Virulent Variant Strain of the above-identified virus for prevention of Porcine Reproductive and Respiratory Syndrome.

The Vaccine as stated above, characterized in that it contains PRRSV whose Nsp2 gene lost nucleotides 1594th-1680th.

The Vaccine as stated above, characterized in that the virus concentration is more than $10^{5.0}$ $TCID_{50}$/ml.

The Vaccine as stated above, characterized in that the virus is inactivated.

The Vaccine as stated above, characterized in that the vaccine is in the form of liquid. The Vaccine further includes excipients commonly used in pharmaceuticals. The exterior appearance of the Vaccine is in the form of milky white emulsion.

The application of the Vaccine as stated above for preparing medicaments to resist the Super-Virulent Variant Strain of Porcine Reproductive and Respiratory Syndrome Virus by immunizing pigs.

The present application also relates to the application of the Vaccine as stated above for preparing medicaments to resist the Super-Virulent Variant Strain (Nsp2 1594th-1680th variant strain) of Porcine Reproductive and Respiratory Syndrome Virus by immunizing pigs.

The present application provides a kind of Vaccine against Porcine Reproductive and Respiratory Syndrome, which includes a Super-Virulent Variant Strain of Porcine Reproductive and Respiratory Syndrome Virus (Nsp2 1594th-1680th variant strain) NVDC-JXA1, Deposit Nos.: CGMCC No. 1964.

The present application further provides a method of preparing Inactivated Vaccine against Super-Virulent Variant Strain (Nsp2 1594th-1680th variant strain) of Porcine Reproductive and Respiratory Syndrome Virus. The method includes as follows:

(1) Reproduction of Seed Virus

The variant strain used for preparing Vaccine was the Super-Virulent Variant Strain (Nsp2 1594th-1680th variant strain) of Porcine Reproductive and Respiratory Syndrome Virus NVDC-JXA1 (Deposit number is CGMCC No. 1964); the concentration of the virus is more than $10^{5.0}$ $TCID_{50}$/ml.

Marc-145 cell strain is preserved in the China Animal Disease Control Center Veterinary Diagnostic Laboratory. The well-grown Marc-145 cells are digested with digestive solution containing trypsin, inoculated in a cell culture flask. The Super-Virulent Variant Strain Virus as stated above is inoculated in the cell culture flask using 1% inoculation amount and incubated at 37° C. The cells are observed for CPE per day. When CPE occurs in more than 70% cells, the virus strain is collected (approximately four days). The cells are frozen-thawed twice, aliquoted and sampled for identification.

(2) Reproduction of Seed Cells

The cell tube is taken from liquid nitrogen tank and thawed in 37° C. water bath. The cells are transferred into a centrifugal tube containing 10 ml serum-free culture medium and centrifuged at 1000 rpm for 5 minutes. The cells are suspended with 10% FBS DMEM culture and incubated with 5% $CO_2$ at 37° C. When coverage rate reaches 100%, the cells are digested with trypsin and pass on from generation to generation proliferation culture according to 1:3.

(3) Preparation of Virus Suspension

Monolayer culture of cells: the seed cells after amplification culture are inoculated in the roller bottle and cultured at a controlled rotational speed of 8 to 9 revolution per hour.

Inoculation: Take the desired number of cells roller bottles with over 80% cell covering rate and get rid of the growth culture medium. Viruses are inoculated in 1% (vol/vol) and cell culture medium containing 2% fetal calf serum is added. The cells of the roller bottles are incubated at 37° C. while rotating.

Harvest: CPE caused by the viruses is observed under microscope. The cell culture is not harvested until CPE occurs in 80 to 90% cells. The cells are frozen-thawed twice and centrifuged for 20 minutes at 3000 g. The cell lyses is reserved as virus suspension.

Inactivation: formaldehyde is added to virus suspension by 0.1% (vol/vol) and mixed well. The above mixture of virus suspension and formaldehyde is incubated at 37° C. in the shaking incubator for 8 hours, taken out, kept at room temperature for 16 hours and stored at 4° C. until use. The retention period is seven days.

(4) Examination of Inactivation Effect

Marc-145 cells are cultured in a 24-well plate. After formation of monolayer of cells, antigen solution inactivated by formaldehyde is inoculated on monolayer of Marc-145 cells by 0.2 ml per well. Each sample is inoculated in three wells. The sample solutions are removed after incubation for 2 hours. The cells are rinsed by maintenance medium and kept on culturing. Meanwhile blank wells are set as control, CPE is observed after 48 hours, 2 generations of blind passagings are made as observed similarly.

(5) Preparation of Vaccine

① Plain Mineral Oil-Adjuvant Vaccine

Preparation of oil phase: White oil for injection (animal use) is heated, then 2% aluminum stearate is added and stirred until dissolved. Then span-80 is added in 6% (vol/vol). The oil phase is sterilized with 121° C. highly compressed steam for 20 minutes until use.

Preparation of water phase: sterilized tween-80 is added in 4% (vol/vol) to inactivated antigen used for preparation of vaccine, the solution stirred until dissolved, which is used as water phase.

Emulsification: the water phase is added slowly to the oil adjuvant in 2:3 (vol/vol). The solution is stirred at 10000 r/min for 4-8 minutes and made into oil-adjuvant inactivated vaccine.

② S206 Oil-Adjuvant Inactivated Vaccine

An inactivated antigen is mixed slowly with S206 adjuvant in 46:54 by low speed stirring and then stirred at 1000 r/min for 10 minutes.

The present invention further provides a Vaccine produced by above methods.

The present application further provides an examination method of PRRSV Vaccine including:

(1) Safety Examination

Each of five healthy and susceptible (neutralizing antibody titer≦4) piglets aged 3 to 4 weeks is injected intramuscularly at the neck area with 4 ml of vaccine. Adverse reaction shouldn't occur after successive observation for 21 days.

(2) Efficacy Examination:

Vaccine immunization is performed according to the following method:

Serum antibody detection and challenge protection test are served as examination methods of immunity efficiency alternatively.

Vaccine immunization: ten piglets aged 4 to 6 weeks are inoculated with the vaccine at a dose of 2 ml per piglet. Similarly ten piglets are set as non-immune control group.

Serum antibody detection: porcine serum is collected before immunization and at the 28th day after immunization. Neutralizing antibody titer of PRRSV variant strain is determined, neutralizing antibody titer of piglets in control group are should be less than or equal 4, at least 8 of immunized pigs should have neutralizing antibody titers greater than or equal to 16.

Challenge protection test: at the 28th day after immunization, each of the pigs is inoculated with 3 ml of PRRSV variant strain diluted 10 times (before diluting the virus concentration is $10^{5.5}$ $TCID_{50}$/ml in the suspension). The pigs are raised and observed for 21 days and killed for autopsy. There should be more than eight infected pigs in control group; there should be more than eight non-ill pigs in immunized group.

Pigs catch the disease should be simultaneously in accordance with the following indexes:

① One of symptoms exists as follows: clinical features such as increased body temperature, weight gain easing up, hemorrhagic spot and cyanopathy in skin, eye conjunctivitis, nervous symptoms including bow kneel prone position, swag of hind body, paralysis, etc.

② One of the following changes is seen by general autopsy: focal hemorrhage, congestion and consolidation of lung started from proximal end of heart leafs, infarction of spleen, lymph node and kidney hemorrhagic spot focus, meninges congestion, etc.

③ One of pathological changes is seen histopathologically as follows: interstitial pneumonia, non-suppurative encephalitis, degenerative change in lymphatic system.

④ PRRSV Super-Virulent Variant Strain is detected in both the pigs that died and the test (killed) pigs by RT-PCR and all the results are positive.

Compared to the prior art, there are advantages of the Inactivated Vaccine against Super-Virulent Variant Strain of Porcine Reproductive and Respiratory Syndrome Virus (PRRSV), of preparation method and application thereof of the present invention as follows:

1. Aspects of the present invention relates to the preparation of Inactivation Vaccine against Super-Virulent Variant Strain of Porcine Reproductive and Respiratory Syndrome Virus and its application for preparing medicines to resist Super-Virulent Variant Strain of Porcine Reproductive and Respiratory Syndrome Virus by immunizing pigs. Preliminary tests demonstrates that the present vaccine has good immuno-protection effect and is able to prevent Porcine Reproductive and Respiratory Syndrome and reduce heavy economic loss suffered by pig husbandry due to Porcine Reproductive and Respiratory Syndrome causing morbidity and mortality of pigs. Therefore, it has good economic and social benefits.

2. The present application further provides a better examination method of PRRSV Vaccine.

EXEMPLARY MODES OF CARRYING OUT THE INVENTION

Example 1

A method for preparing Inactivated Vaccine against Variant Strain of PRRSV including:

(1) Reproduction of Seed Virus

The strain used for preparing Vaccine was the Super-Virulent Variant Strain (Nsp2 1594th-1680th deletion variant strain) of Porcine Reproductive and Respiratory Syndrome Virus NVDC-JXA1 (Deposit number is CGMCC No. 1964).

Cell: Marc-145 cell strain, preserved in the China Animal Disease Control Center Veterinary Diagnostic Laboratory, passaging batch are 11st, 15th and 20th.

The well-grown Marc-145 cells were digested with trypsin and digestion solution, inoculated in a cell culture flask. The Super-Virulent Variant Strain Virus as stated above was inoculated in the cell culture flask using 1% inoculation amount and incubated at 37° C. The cells were observed for Cytopathic effect (CPE) per day. The virus strain was collected (approximately four days) when CPE occurs in more than 70% cells. The cells were frozen-thawed twice, aliquoted and sampled for identification.

(2) Reproduction of Seed Cells

The cell tube was taken from liquid nitrogen tank and thawed in 37° C. water bath. The cells were transferred into a centrifuge tube containing 10 ml serum-free culture medium and centrifuged at 1000 rpm for 5 minutes. The cells were suspended with 10% FBS DMEM culture and incubated with 5% $CO_2$ at 37° C. When coverage rate reaches 100%, the cells were digested with trypsin and pass on from generation to generation proliferation culture according to 1:3.

(3) Preparation of Virus Suspension

Monolayer culture of cells: the seed cells after amplification culture were inoculated in the roller bottle and cultured at a controlled rotational speed of 8 to 9 revolution per hour.

Inoculation: took the desired number of cell roller bottles with over 80% cell coverage rate and got rid of the growth culture medium. The viruses are inoculated in 1% (vol/vol) and cell culture medium containing 2% fetal calf serum is added. The cells were incubated at 37° C. while rotating the roller bottles.

Harvest: CPE caused by the viruses was observed under microscope. The cell culture was not harvested until CPE occurs in 80 to 90% cells. The cells were frozen-thawed twice and centrifuged for 20 minutes at 3000 g. The cell lyses was reserved as virus suspension.

Inactivation: formaldehyde was added to virus suspension by 0.1% (vol/vol) and mixed well. The above mixture of virus suspension and formaldehyde was incubated at 37° C. in the shaking incubator for 8 hours, taken out, kept at room temperature for 16 hours and stored at 4° C. until use.

(4) Examination of Inactivation Effect

Marc-145 cells were cultured in a 24-well plate. Until forming monolayer of cells, five batches of antigen solution inactivated by Formaldehyde were inoculated on monolayer of Marc-145 cells by 0.2 ml per well. Each sample was inoculated in three wells. The sample solutions were removed after incubation for 2 hours. The cells were rinsed by maintenance medium and kept on culturing. Meanwhile blank wells were set as control, CPE was observed after 48 hours, 2 generations of blind passagings were made as observed similarly.

(5) Preparation of Vaccine

① Plain Mineral Oil-Adjuvant Vaccine

Preparation of oil phase: White oil for injection (animal use) was heated, then 2% aluminum stearate was added and stirred until dissolved. Then span-80 was added in 6% (vol/vol). The oil phase was sterilized with 121° C. highly compressed steam for 20 minutes until use.

Preparation of water phase: sterilized tween-80 was added to inactivated antigen by 4% (vol/vol) used for preparation of vaccine, stirred the solution until completely dissolved, which was used as water phase.

Emulsification: the water phase was added slowly to the oil adjuvant in 2:3 (vol/vol). The solution was stirred at 10000 r/min for 4-8 minutes and made into oil-adjuvant inactivated vaccine.

② S206 Oil-Adjuvant Inactivated Vaccine

An inactivated virus antigen was mixed slowly with S206 oil-adjuvant in 46:54 by low speed stirring and then stirred at 1000 r/min for 10 minutes.

Example 2

Safety Test of Vaccine (1) Vaccine and Experimental Animals

Three batches of Inactivated Vaccine of PRRSV Variant Strain were prepared, the batch number were 2007001, 2007002 and 2007003. The healthy pigs were examined with negative result for PRRSV antibody test, the healthy pigs were provided by Inner Mongolia Biopharmaceutical Factory.

(2) Youngest Day-Old Animals were Inoculated with One Dose of Vaccine One Time

Five healthy 3 week-old pigs were immunized with each batch of Vaccines respectively. Each pig was injected intramuscularly at the neck area with 2 ml Vaccine, raised and observed for 21 days. The animals' reaction was observed after immunization and some of the pigs were dissected. The absorption conditions of injection sites Vaccine were observed.

(3) Target Animals were Inoculated with One Dose of Vaccine Repeatedly:

Five healthy 3-4 week-old pigs were immunized with each batch of Vaccines respectively. Each pig was injected intramuscularly at the neck area with 2 ml Vaccine. After three weeks the immunization was performed again and each pig was injected again at the neck muscle area with 2 ml Vaccine. The pigs were raised and observed for 21 days. The animals' reaction was observed after injection. Some of the pigs were dissected. The absorption conditions of injection sites Vaccine were observed.

(4) Target Animals were Inoculated with One Overdose of Vaccine:

Five healthy 3-4 week-old pigs were immunized with each batch of Vaccines respectively. Each pig was injected intramuscularly at the neck area with 4 ml Vaccine, raised and observed for 21 days. The animals' reaction was observed after immunization. Some of the pigs were dissected. The absorption conditions of injection sites Vaccine were observed.

(5) Assay Results

No local or whole-body adverse reactions were found on pigs in the test groups and control groups mentioned above. After having been injected with Vaccine the animals showed good mental status and appetite. The dissection results of some of the pigs showed that no symptom such as red swelling and suppuration were found in injection site of Vaccine and the Vaccine was absorbed completely. Therefore three batches of the Vaccine are safe for pigs under the conditions of one dose, overdose and multi-inoculation.

The results were shown in table 1 as follows:

TABLE 1

Results of Safety Test

| Test group | Vaccine batch | animal age | number of animals (per) | adverse reaction | anatomic change |
|---|---|---|---|---|---|
| inoculated with one dose one time on youngest day-old animals | 2007001 | 3 weeks | 5 | no adverse reaction | No pathological change found, vaccine absorbed fully |
|  | 2007002 | 3-4 weeks | 5 | no adverse reaction | No pathological change found, vaccine absorbed fully |
|  | 2007003 | 3-4 weeks | 5 | no adverse reaction | No pathological change found, vaccine absorbed fully |
| inoculated with one dose repeatedly | 2007001 | 3-4 weeks | 5 | no adverse reaction | No pathological change found, vaccine absorbed fully |
|  | 2007002 | 3-4 weeks | 5 | no adverse reaction | No pathological change found, vaccine absorbed fully |
|  | 2007003 | 3-4 weeks | 5 | no adverse reaction | No pathological change found, vaccine absorbed fully |
| Inoculated with overdose | 2007001 | 3-4 weeks | 5 | no adverse reaction | No pathological change found, vaccine absorbed fully |
|  | 2007002 | 3-4 weeks | 5 | no adverse reaction | No pathological change found, vaccine absorbed fully |
|  | 2007003 | 3-4 weeks | 5 | no adverse reaction | No pathological change found, vaccine absorbed fully |

Example 3

Efficacy Test of Vaccine (1) Vaccine and Experimental Animal

Three batches of Inactivated Vaccine of PRRSV Variant Strain were prepared, the batch number were 2007001, 2007002 and 2007003. The healthy pigs were examined with negative result for PRRSV antibody test, the healthy pigs were provided by Inner Mongolia Biopharmaceutical Factory.

(2) Vaccine Immunization:

Ten 40±5 day-old piglets were inoculated with three batches of vaccine with a dose of 2 ml per piglet. Meanwhile ten piglets were set as non-immunization control group.

(3) Serum Antibody Detection:

Porcine serum was collected at the 28th day after immunization. Neutralizing Antibody Titre of PRRSV variant strain was determined by cell neutralization test.

(4) Challenge Test:

At the 28th day after immunization, the pigs were challenged with PRRSV Super-Virulent Variant Strain (Nsp2 1594th-1680th deletion variant) NVDC-JXA1. Virus suspension with concentration of $10^{5.9}$ $TCID_{50}$/ml was diluted 10 times. The pigs were inoculated via muscle of neck with a dose of 3 ml per head. The pigs were fed and observed for 21 days. Reactions of animals including body temperature, clinical symptoms, periodical serum test, and general pathological changes of autopsy in each group were recorded. Regarding dead pigs and test pigs killed at the 21st day, PRRSV Variant Strains were determined by RT-PCR.

(5) Determination Results of Serum Antibody:

At the 28th day after immunization with three batches of Vaccine, i.e. before challenge, neutralizing antibody titers of each immunized group against PRRSV Super-Virulent Variant Strain all reached over 16, serum antibody of control groups were all negative, see details in table 2 as follows:

TABLE 2

Determination results of serum antibody

| Test group | Vaccine batch | neutralizing antibody titer |
|---|---|---|
| Immunized group 1 | 2007001 | 16, 32, 32, 32, 64, 128, 64, 64, 32, 64 |
| Immunized group 2 | 2007002 | 64, 64, 32, 32, 128, 64, 128, 64, 128, 16 |
| Immunized group 3 | 2007003 | 128, 16, 64, 64, 64, 64, 32, 128, 32, 64 |
| Control group |  | <4, <4, <4, <4, <4, <4, <4, <4, <4, <4 |

(6) Results of Challenge Test

1) Pigs in Control Group:

After challenge all ten pigs suffered disease, and four pigs died.

Diseased pigs have symptoms as follows: ① Clinical features such as increased body temperature, hemorrhagic spot and cyanopathy in skin, eye conjunctivitis, nervous symptoms including bow kneel prone position, deviation of hind body, paralysis, etc. ② The following changes are seen by general autopsy: focal hemorrhage, congestion and consolidation of lung started from proximal end of heart leafs, infarction of spleen, lymph node and kidney hemorrhagic spot focus, meninges congestion, etc. ③ Pathological changes are seen histopathologically as follows: interstitial pneumonia, non-suppurative encephalitis, degenerative change in lymphatic system.

For dead pigs and contrast group test pigs killed after observation for 21 days, PRRSV variant strain were detected by RT-PCR and all the results are positive. Details in table 3 as follows:

TABLE 3

Results of challenge test

| Animal number | Onset time of disease (DPI) | Death time (DPI) | symptoms | General pathological changes | histology | RT-PCR |
|---|---|---|---|---|---|---|
| Cont. 1 | 3 | Not dead, killed | increased body temperature, skin cyanopathy, nervous symptoms | lung consolidation, hemorrhagic spot in lymph node and kidney, meninges congestion etc. | interstitial pneumonia, degenerative change in lymphatic system | + |
| Cont. 2 | 3 | 7 | increased body temperature, hemorrhagic spot and cyanopathy in skin, eye conjunctivitis, nervous symptoms | hemorrhage, congestion and consolidation of lung, kidney hemorrhagic spot focus, meninges congestion etc. | interstitial pneumonia, non-suppurative encephalitis | + |
| Cont. 3 | 3 | 8 | increased body temperature, skin hemorrhagic spot, nervous symptoms | hemorrhage, congestion and consolidation of lung, kidney hemorrhagic spot focus, meninges congestion etc. | interstitial pneumonia, non-suppurative encephalitis | + |
| Cont. 4 | 4 | Not dead, killed | increased body temperature, hemorrhagic spot and cyanopathy in skin, eye conjunctivitis, nervous symptoms | congestion and consolidation of lung, lymph node and kidney hemorrhagic spot focus, meninges congestion etc. | interstitial pneumonia, non-suppurative encephalitis, degenerative change in lymphatic system | + |
| Cont. 5 | 3 | Not dead, killed | increased body temperature, skin hemorrhagic spot, nervous symptoms | hemorrhage, congestion and consolidation of lung, kidney hemorrhagic spot focus, meninges congestion etc. | interstitial pneumonia, non-suppurative encephalitis, degenerative change in lymphatic system | + |
| Cont. 6 | 3 | 9 | increased body temperature, skin hemorrhagic spot, nervous symptoms | hemorrhage, congestion and consolidation of lung, kidney hemorrhagic spot focus, meninges congestion etc. | interstitial pneumonia, non-suppurative encephalitis | + |
| Cont. 7 | 3 | Not dead, killed | increased body temperature, skin hemorrhagic | hemorrhage, congestion and consolidation of lung, kidney hemorrhagic spot | interstitial pneumonia, non-suppurative encephalitis, | + |

TABLE 3-continued

Results of challenge test

| Animal number | Onset time of disease (DPI) | Death time (DPI) | symptoms | General pathological changes | histology | RT-PCR |
|---|---|---|---|---|---|---|
| Cont. 8 | 4 | 8 | spot, nervous symptoms increased body temperature, skin hemorrhagic spot, nervous symptoms | focus, meninges congestion etc. hemorrhage, congestion and consolidation of lung, kidney hemorrhagic spot focus, meninges congestion etc. | degenerative change in lymphatic system interstitial pneumonia, non-suppurative encephalitis | + |
| Cont. 9 | 4 | Not dead, killed | increased body temperature, skin hemorrhagic spot, nervous symptoms | congestion and consolidation of lung,, kidney hemorrhagic spot focus, meninges congestion etc. | interstitial pneumonia, degenerative change in lymphatic system | + |
| Cont. 10 | 3 | Not dead, killed | increased body temperature, skin hemorrhagic spot, nervous symptoms | congestion of lungs, lymph node consolidation, kidney and lymph node hemorrhagic spot focus, meninges congestion etc. | interstitial pneumonia, degenerative change in lymphatic system | + |

2) Vaccine Immunized Group

In test groups immunized respectively with three batches of Inactivated Vaccine of PRRSV Variant strain, no adverse reactions or disease occurred. After observation for 21 days, test pigs were killed and PRRSV Super-Virulent Variant strain were detected by RT-PCR showing all negative results. The results demonstrated that the Vaccine against PRRSV Super-Virulent Variant strain can produce good immunity by immunizing pigs with the Inactivated Vaccine of PRRSV Super-Virulent Variant strain. Results were shown in table 4 as follows:

TABLE 4

Immunization Effect of vaccination

| Test group | Vaccine batch | Animal number (head) | Adverse reaction | Disease Onset number | Death number | RT-PCR determination | Protected animal number (per) |
|---|---|---|---|---|---|---|---|
| 1 | 2007001 | 10 | no | 0 | 0 | All negative | 10 |
| 2 | 2007002 | 10 | no | 0 | 0 | All negative | 10 |
| 3 | 2007003 | 10 | no | 0 | 0 | All negative | 10 |

Example 4

Determination Method Test (1) Vaccine and Experimental Animals

Inactivated Vaccine of PRRSV Variant strain with batch number of 2007000;

Five healthy and susceptible piglets aged 3 to 4 weeks, twenty healthy and susceptible piglets aged 4 to 6 weeks, provided by Inner Mongolia Biopharmaceutical Factory, PRRSV antibody were negative via detecting (neutralizing antibody titer≦4).

(2) Safety Examination

Each piglet was injected intramuscularly at the neck area with 4 ml Vaccine. Adverse reaction and anatomic changes were recorded after successive observation for 21 days.

(3) Efficacy Examination:

① Vaccine Immunization:

Ten piglets aged 4 to 6 weeks were inoculated with Vaccine at a dose of 2 ml per piglet respectively. Meanwhile ten piglets were set as non-immunization control group;

② Serum antibody detection: piglet serum was collected at the 28th day after and before immunization. Neutralizing antibody titre against PRRSV Variant strain was determined.

③ Challenge protection test: at the 28th day after immunization, each pig was intramuscularly inoculated with 3 ml PRRSV variant diluted 10 times (before diluting virus suspension with concentration of $10^{5.5}$ $TCID_{50}$/ml), fed and observed for further 21 days and killed for autopsy.

(4) Determination Results of Safety

At the 21st day after vaccination, no adverse reaction occurred in all of five test pigs aged 3 to 4 week, no pathological change was seen after autopsy. Results were shown in table 5:

TABLE 5

Determination results of safety

| Animal number | Animal week old | Adverse Reaction | Anatomic change |
|---|---|---|---|
| S1 | 3 weeks | no adverse reaction | no pathological change, vaccine absorbed fully |
| S2 | 4 weeks | no adverse reaction | no pathological change, vaccine absorbed fully |
| S3 | 3.5 weeks | no adverse reaction | no pathological change, vaccine absorbed fully |
| S4 | 3 weeks | no adverse reaction | no pathological change, vaccine absorbed fully |
| S5 | 4 weeks | no adverse reaction | no pathological change, vaccine absorbed fully |

(5) Determination Results of Efficacy Test:

Ten pigs in immunized group were tested at the 28th day. Neutralizing antibody titers all reached over 16. After challenge no disease onset and death were found on the pigs observed for 21 days. PRRSV Super-Virulent Variant strain were detected by RT-PCR and all the results are negative.

All of ten pigs in challenge control group caught the disease at 3rd to 5th day after inoculation with the virus. Five diseased pigs died. Positive results of PRRSV Super-Virulent Variant strain were detected by RT-PCR. Details were shown in table 6.

(6) Standards for Identifying Onset Disease of Pigs:

Diseased pigs should be judged simultaneously in accordance with the following indexes:

① One of symptoms exists as follows: clinical features such as increased body temperature, retardation of weight gain, hemorrhagic spot and cyanopathy in skin, eye conjunctivitis, nervous symptoms including bow kneel prone position, swaying of hind quarter, paralysis, etc.

② One of the following changes is seen by general autopsy: focal hemorrhage, congestion and consolidation of lungs started from proximal end of heart leafs, infarction of spleen, lymph node and kidney hemorrhagic spot focus, meninges congestion, etc.

③ One of pathological changes is seen histopathologically as follows: interstitial pneumonia, non-suppurative encephalitis, degenerative change in lymphatic system.

④ PRRSV Super-Virulent Variant Strain in dead pigs and killed pigs is detected by RT-PCR and all the results are positive.

TABLE 6

Results of efficacy test

| | animal number | Onset time of disease (DPI) | death time (DPI) | macroscopical health status | general pathological change of autopsy | histology determination result | antibody titer | RT-PCR |
|---|---|---|---|---|---|---|---|---|
| Vaccination group | Vac. 1 | no onset of disease | no died | healthy | no pathological change found | no pathological change | 64 | − |
| | Vac. 2 | no onset of disease | no died | healthy | no pathological change found | no pathological change | 128 | − |
| | Vac. 3 | no onset of disease | no died | healthy | no pathological change found | no pathological change | 32 | − |
| | Vac. 4 | no onset of disease | no died | healthy | no pathological change found | no pathological change | 32 | − |
| | Vac. 5 | no onset of disease | no died | healthy | no pathological change found | no pathological change | 64 | − |
| | Vac. 6 | no onset of disease | no died | healthy | no pathological change found | no pathological change | 16 | − |
| | Vac. 7 | no onset of disease | no died | healthy | no pathological change found | no pathological change | 32 | − |
| | Vac. 8 | no onset of disease | no died | healthy | no pathological change found | no pathological change | 16 | − |
| | Vac. 9 | no onset of disease | no died | healthy | no pathological change found | no pathological change | 64 | − |
| | Vac. 10 | no onset of disease | no died | healthy | no pathological change found | no pathological change | 32 | − |
| Challenge control group | Cont. 1 | 3 | 7 | increased body temperature, hemorrhagic spot and cyanopathy in skin, eye conjunctivitis, nervous symptoms | hemorrhage, congestion and consolidation of lung, kidney hemorrhagic spot focus, meninges congestion etc. | interstitial pneumonia, degenerative change in lymphatic system | not determined | + |
| | Cont. 2 | 3 | not dead, killed | increased body temperature, skin cyanopathy, nervous symptoms | lung consolidation, hemorrhagic spot in lymph node and kidney, meninges congestion etc. | interstitial pneumonia, non-suppurative encephalitis | not determined | + |
| | Cont. 3 | 3 | not dead, killed | increased body temperature, skin hemorrhage, nervous symptoms | hemorrhage, congestion and consolidation of lung, kidney hemorrhagic spot focus, meninges congestion etc. | interstitial pneumonia, non-suppurative encephalitis, degenerative change in lymphatic system | not determined | + |
| | Cont. 4 | 5 | not dead, killed | increased body temperature, skin cyanopathy, nervous symptoms | lung consolidation, hemorrhagic spot in lymph node and kidney, meninges congestion etc. | interstitial pneumonia, non-suppurative encephalitis | not determined | + |
| | Cont. 5 | 3 | 8 | increased body temperature, skin hemorrhage, nervous symptoms | hemorrhage, congestion and consolidation of lung, kidney hemorrhagic spot focus, meninges congestion etc. | interstitial pneumonia, non-suppurative encephalitis | not determined | + |
| | Cont. 6 | 3 | 9 | increased body temperature, skin hemorrhage, nervous symptoms | hemorrhage, congestion and consolidation of lung, kidney hemorrhagic spot focus, | interstitial pneumonia, non-suppurative encephalitis | not determined | + |

TABLE 6-continued

Results of efficacy test

| animal number | Onset time of disease (DPI) | death time (DPI) | macroscopical health status | general pathological change of autopsy | histology determination result | antibody titer | RT-PCR |
|---|---|---|---|---|---|---|---|
| Cont. 7 | 4 | 10 | increased body temperature, skin hemorrhage, nervous symptoms | meninges congestion etc. hemorrhage, congestion and consolidation of lung, kidney hemorrhagic spot focus, meninges congestion etc. | interstitial pneumonia, non-suppurative encephalitis, degenerative change in lymphatic system | not determined | + |
| Cont. 8 | 4 | not dead, killed | increased body temperature, skin hemorrhage, nervous symptoms | congestion of lung, lymph node consolidation, kidney and lymph node hemorrhagic spot focus, meninges congestion etc. | interstitial pneumonia, degenerative change in lymphatic system | not determined | + |
| Cont. 9 | 4 | not dead, killed, | increased body temperature, skin hemorrhage, nervous symptoms | congestion and consolidation of lung,, kidney hemorrhagic spot focus, meninges congestion etc. | interstitial pneumonia, degenerative change in lymphatic system | not determined | + |
| Cont. 10 | 4 | 8 | increased body temperature, skin hemorrhage, nervous symptoms | hemorrhage, congestion and consolidation of lung, kidney hemorrhagic spot focus, meninges congestion etc. | interstitial pneumonia, non-suppurative encephalitis | not determined | + |

The invention claimed is:

1. A Variant Strain of Porcine Reproductive and Respiratory Syndrome Virus (PRRSV), characterized in that nucleotides 1594th-1680th are deleted in the virus Nsp2 gene, Virus Deposit Number is: CGMCC No. 1964.

2. An inactivated vaccine for prevention of Porcine Reproductive and Respiratory Syndrome, characterized in that the vaccine contains the Variant Strain of PRRSV of claim 1.

3. The Vaccine according to claim 2, characterized in that the virus concentration is more than $10^{5.0}$ TCID$_{50}$/ml.

4. The Vaccine according to claim 2, characterized in that the Vaccine is in the form of liquid.

5. The method of preparing the inactivated vaccine according to claim 2, comprising:
(1) reproducing a seed virus of the variant strain of PRRSV of claim 1;
(2) reproducing seed cells;
(3) preparing a virus suspension;
(4) examining inactivation effect; and
(5) preparing the vaccine.

* * * * *